United States Patent
Koehler (10) Patent No.: US 10,022,212 B2
(45) Date of Patent: Jul. 17, 2018

(54) TEMPORARY VENOUS FILTER WITH ANTI-COAGULANT DELIVERY METHOD

(75) Inventor: Cleve Koehler, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 282 days.

(21) Appl. No.: 13/005,957

(22) Filed: Jan. 13, 2011

(65) Prior Publication Data

US 2012/0184984 A1    Jul. 19, 2012

(51) Int. Cl.
*A61F 2/01*    (2006.01)

(52) U.S. Cl.
CPC .......... *A61F 2/01* (2013.01); *A61F 2002/016* (2013.01); *A61F 2230/005* (2013.01); *A61F 2230/008* (2013.01); *A61F 2230/0067* (2013.01); *A61F 2250/0067* (2013.01)

(58) Field of Classification Search
CPC ............... A61F 2/01; A61F 2250/0067; A61F 2230/008; A61F 2002/016; A61F 2002/018; A61F 2/013
USPC ... 606/200, 191, 192, 509, 33, 12, 157–159; 128/897–899; 604/105–109
See application file for complete search history.

(56) References Cited

U.S. PATENT DOCUMENTS

| | | |
|---|---|---|
| 2,281,448 A | 4/1942 | Mathey |
| 3,137,298 A | 6/1964 | Glassman |
| 3,174,851 A | 3/1965 | Buehler |
| 3,334,629 A | 8/1967 | Cohn |
| 3,540,431 A | 11/1970 | Mobin-Uddin |
| 3,868,956 A | 3/1975 | Alfidi et al. |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,655,771 A | 4/1987 | Wallsten |
| 4,665,906 A | 5/1987 | Jervis |
| 4,688,553 A | 8/1987 | Metals |
| 4,727,873 A | 3/1988 | Mobin-Uddin |
| 4,759,757 A | 7/1988 | Pinchuk |
| 4,781,177 A | 11/1988 | Lebigot |

(Continued)

FOREIGN PATENT DOCUMENTS

| | | |
|---|---|---|
| DE | 003417738 | 11/1985 |
| DE | 3429850 A1 | 2/1986 |

(Continued)

OTHER PUBLICATIONS

Morris Simon, M.D. et al., A Vena Cava Filter Using Thermal Shape Memory Alloy, Oct. 1977, 89-94.

(Continued)

*Primary Examiner* — Katrina Stransky
(74) *Attorney, Agent, or Firm* — Brinks Gilson & Lione (57) ABSTRACT

The present invention provides a removable vena cava filter for capturing and treating blood clots in a blood vessel. The filter comprises a hub, a plurality of struts extending distally from the hub, and a tubular member disposed through the hub. The tubular member has a proximal end and a distal portion including a plurality of perforations. A catheter may be attached to the proximal end of the tubular member. Fluid may be injected into the catheter to treat blood clots captured in the filter.

19 Claims, 8 Drawing Sheets

(56) References Cited

U.S. PATENT DOCUMENTS

| | | |
|---|---|---|
| 4,793,348 A | 12/1988 | Palmaz |
| 4,817,600 A | 4/1989 | Herms et al. |
| 4,830,003 A | 5/1989 | Wolff et al. |
| 4,832,055 A | 5/1989 | Palestrant |
| 4,856,516 A | 8/1989 | Hillstead |
| 4,873,978 A | 10/1989 | Ginsburg |
| 4,943,297 A | 7/1990 | Saveliev et al. |
| 4,950,227 A | 8/1990 | Savin et al. |
| 4,954,126 A | 9/1990 | Wallsten |
| 4,957,501 A | 9/1990 | Lahille et al. |
| 4,969,891 A | 11/1990 | Gewertz |
| 4,990,156 A | 2/1991 | Lefebvre |
| 5,037,377 A | 8/1991 | Alonso |
| 5,059,205 A | 10/1991 | Ei-Nounou et al. |
| 5,061,275 A | 10/1991 | Wallsten et al. |
| 5,067,957 A | 11/1991 | Jervis |
| 5,071,407 A | 12/1991 | Termin et al. |
| 5,108,418 A | 4/1992 | Lefebvre |
| 5,108,419 A | 4/1992 | Reger et al. |
| 5,133,733 A | 7/1992 | Rasmussen et al. |
| 5,135,516 A | 8/1992 | Sahatjian et al. |
| 5,147,379 A | 9/1992 | Sabbaghian et al. |
| 5,152,777 A | 10/1992 | Goldberg et al. |
| 5,160,342 A | 11/1992 | Reger et al. |
| 5,190,546 A | 3/1993 | Jervis |
| 5,217,484 A | 6/1993 | Marks |
| 5,221,261 A | 6/1993 | Termin et al. |
| 5,224,953 A | 7/1993 | Morgentaler |
| 5,234,458 A | 8/1993 | Metais |
| 5,242,462 A | 9/1993 | El-Nounou et al. |
| 5,304,121 A | 4/1994 | Sahatjian |
| 5,304,200 A | 4/1994 | Spaulding |
| 5,324,304 A | 6/1994 | Rasmussen |
| 5,329,942 A | 7/1994 | Gunther et al. |
| 5,300,086 A | 8/1994 | Gory et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,421,832 A | 6/1995 | Lefebvre |
| 5,413,586 A | 9/1995 | Dibie et al. |
| 5,476,508 A | 12/1995 | Amstrup |
| 5,527,338 A | 6/1996 | Purdy |
| 5,536,242 A * | 7/1996 | Willard et al. ............... 604/30 |
| 5,540,712 A | 7/1996 | Kleshinski et al. |
| 5,549,626 A | 8/1996 | Miller et al. |
| 5,549,629 A | 8/1996 | Thomas et al. |
| 5,601,595 A | 2/1997 | Smith |
| 5,626,605 A | 5/1997 | Irie et al. |
| 5,630,801 A | 5/1997 | Roussigne et al. |
| 5,634,942 A | 6/1997 | Chevillon et al. |
| 5,649,906 A | 7/1997 | Gory et al. |
| 5,649,953 A | 7/1997 | Lefebvre |
| 5,669,933 A | 9/1997 | Simon et al. |
| 5,681,347 A | 10/1997 | Cathcart et al. |
| 5,683,411 A | 11/1997 | Kavteladze et al. |
| 5,695,519 A | 12/1997 | Summers et al. |
| 5,709,704 A | 1/1998 | Nott et al. |
| 5,720,764 A | 2/1998 | Naderlinger |
| 5,725,550 A | 3/1998 | Nadal |
| 5,746,767 A | 5/1998 | Smith |
| 5,755,778 A | 5/1998 | Kleshinski |
| 5,755,790 A | 5/1998 | Chevillon et al. |
| 5,776,162 A | 7/1998 | Kleshinski |
| 5,800,457 A | 9/1998 | Gelbfish |
| 5,800,525 A | 9/1998 | Bachinski et al. |
| 5,807,398 A | 9/1998 | Shaknovich |
| 5,810,874 A * | 9/1998 | Lefebvre ............... 606/200 |
| 5,836,968 A | 11/1998 | Simon et al. |
| 5,836,969 A | 11/1998 | Kim et al. |
| 5,843,244 A | 12/1998 | Pelton et al. |
| 5,853,420 A | 12/1998 | Chevillon et al. |
| 5,895,399 A | 4/1999 | Barbut et al. |
| 5,902,317 A | 5/1999 | Kleshinski et al. |
| 5,916,235 A | 6/1999 | Guglielmi |
| 5,928,260 A | 7/1999 | Chin et al. |
| 5,928,261 A | 7/1999 | Ruiz |
| 5,932,035 A | 8/1999 | Koger et al. |
| 5,938,683 A | 8/1999 | Lefebvre |
| 5,951,585 A | 9/1999 | Cathcart et al. |
| 5,961,546 A | 10/1999 | Robinson et al. |
| 5,976,172 A | 11/1999 | Homsma et al. |
| 5,984,947 A | 11/1999 | Smith |
| 6,001,118 A * | 12/1999 | Daniel et al. ............... 606/200 |
| 6,007,557 A | 12/1999 | Ambrisco et al. |
| 6,007,558 A * | 12/1999 | Ravenscroft et al. ......... 606/200 |
| 6,013,093 A | 1/2000 | Nott et al. |
| 6,077,274 A | 6/2000 | Ouchi et al. |
| 6,080,178 A | 6/2000 | Meglin |
| 6,086,610 A | 7/2000 | Duerig et al. |
| 6,126,673 A | 10/2000 | Kim et al. |
| 6,129,755 A | 10/2000 | Mathis et al. |
| 6,146,404 A | 11/2000 | Kim et al. |
| 6,152,144 A | 11/2000 | Lesh et al. |
| 6,156,055 A | 12/2000 | Ravenscroft |
| 6,156,061 A | 12/2000 | Wallace et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,193,739 B1 | 2/2001 | Chevillon et al. |
| 6,221,102 B1 | 4/2001 | Baker et al. |
| 6,231,589 B1 | 5/2001 | Wessman et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,088 B1 | 6/2001 | Lowery |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,900 B1 | 8/2001 | Nott et al. |
| 6,273,901 B1 | 8/2001 | Whitcher et al. |
| 6,277,139 B1 | 8/2001 | Levinson et al. |
| 6,287,315 B1 | 9/2001 | Wijeratne et al. |
| 6,287,329 B1 | 9/2001 | Duerig et al. |
| 6,306,163 B1 | 10/2001 | Fitz |
| 6,312,454 B1 | 11/2001 | Stockel et al. |
| 6,312,455 B2 | 11/2001 | Duerig et al. |
| 6,325,815 B1 | 12/2001 | Kusleika et al. |
| 6,331,183 B1 | 12/2001 | Suon |
| 6,342,062 B1 | 1/2002 | Suon et al. |
| 6,342,063 B1 | 1/2002 | DeVries et al. |
| 6,342,067 B1 | 1/2002 | Mathis et al. |
| 6,346,116 B1 | 2/2002 | Brooks et al. |
| 6,364,895 B1 | 4/2002 | Greenhalgh |
| 6,383,206 B1 * | 5/2002 | Gillick et al. ............... 606/200 |
| 6,391,044 B1 | 5/2002 | Yadav et al. |
| 6,391,045 B1 | 5/2002 | Kim et al. |
| 6,436,120 B1 | 8/2002 | Meglin |
| 6,436,121 B1 | 8/2002 | Blom |
| 6,447,530 B1 | 9/2002 | Ostrovsky et al. |
| 6,461,370 B1 | 10/2002 | Gray et al. |
| 6,468,290 B1 | 10/2002 | Weldon et al. |
| 6,482,222 B1 | 11/2002 | Bruckheimer et al. |
| 6,485,502 B2 | 11/2002 | DonMichael et al. |
| 6,506,205 B2 | 1/2003 | Goldberg et al. |
| 6,511,503 B1 | 1/2003 | Burkett et al. |
| 6,517,559 B1 | 2/2003 | O'Connell |
| 6,527,962 B1 | 3/2003 | Nadal |
| 6,540,767 B1 | 4/2003 | Walak et al. |
| 6,551,342 B1 | 4/2003 | Shen et al. |
| 6,558,404 B2 | 5/2003 | Tsukernik |
| 6,569,183 B1 | 5/2003 | Kim et al. |
| 6,579,303 B2 | 6/2003 | Amplatz |
| 6,582,447 B1 | 6/2003 | Patel et al. |
| 6,589,266 B2 | 7/2003 | Whitcher et al. |
| 6,599,307 B1 | 7/2003 | Huter et al. |
| 6,602,226 B1 | 8/2003 | Smith et al. |
| 6,616,680 B1 | 9/2003 | Thielen |
| 6,638,294 B1 | 10/2003 | Palmer |
| 6,652,558 B2 | 11/2003 | Patel et al. |
| 6,663,652 B2 * | 12/2003 | Daniel et al. ............... 606/200 |

(56) References Cited

U.S. PATENT DOCUMENTS

| | | |
|---|---|---|
| 6,685,722 B1 | 2/2004 | Rosenbluth et al. |
| 6,706,054 B2 | 3/2004 | Wessman et al. |
| 6,726,621 B2 | 4/2004 | Suon et al. |
| 6,972,025 B2 | 12/2005 | WasDyke |
| 7,056,286 B2* | 6/2006 | Ravenscroft et al. ........ 600/200 |
| 7,077,854 B2 | 7/2006 | Khosravi |
| 7,297,000 B1 | 11/2007 | Bernard |
| 7,625,390 B2 | 12/2009 | Osborne et al. |
| 7,699,867 B2 | 4/2010 | Osborne et al. |
| 8,469,970 B2* | 6/2013 | Diamant et al. ............. 606/127 |
| 2001/0000799 A1* | 5/2001 | Wessman et al. ............ 606/200 |
| 2001/0011181 A1 | 8/2001 | DiMatteo |
| 2001/0023358 A1 | 9/2001 | Tsukernik |
| 2001/0034547 A1 | 10/2001 | Hall et al. |
| 2001/0034548 A1 | 10/2001 | Vrba et al. |
| 2001/0037126 A1 | 11/2001 | Stack et al. |
| 2001/0039432 A1 | 11/2001 | Whitcher et al. |
| 2002/0002401 A1 | 1/2002 | McGuckin, Jr. et al. |
| 2002/0016624 A1 | 2/2002 | Patterson et al. |
| 2002/0032460 A1 | 3/2002 | Kusleika et al. |
| 2002/0039445 A1 | 4/2002 | Abe et al. |
| 2002/0055767 A1 | 5/2002 | Forde et al. |
| 2002/0087187 A1 | 7/2002 | Mazzocchi et al. |
| 2002/0099431 A1 | 7/2002 | Armstrong et al. |
| 2002/0116024 A1 | 8/2002 | Goldberg et al. |
| 2002/0133217 A1 | 9/2002 | Sirhan et al. |
| 2002/0138097 A1 | 9/2002 | Ostrovsky et al. |
| 2002/0156520 A1 | 10/2002 | Boylan et al. |
| 2002/0161393 A1 | 10/2002 | Demond et al. |
| 2002/0169474 A1 | 11/2002 | Kusleika et al. |
| 2002/0169495 A1 | 11/2002 | Gifford et al. |
| 2002/0183782 A1 | 12/2002 | Tsugita et al. |
| 2002/0193827 A1 | 12/2002 | McGuckin, Jr. et al. |
| 2002/0193828 A1 | 12/2002 | Griffin et al. |
| 2002/0193874 A1 | 12/2002 | Crowley |
| 2003/0018343 A1 | 1/2003 | Mathis |
| 2003/0028238 A1 | 2/2003 | Burkett et al. |
| 2003/0040772 A1 | 2/2003 | Hyodoh et al. |
| 2003/0055481 A1 | 3/2003 | McMorrow |
| 2003/0069596 A1 | 4/2003 | Eskuri |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0097145 A1 | 5/2003 | Goldberg et al. |
| 2003/0105484 A1 | 6/2003 | Boyle et al. |
| 2003/0109897 A1 | 6/2003 | Walak et al. |
| 2003/0114880 A1 | 6/2003 | Hansen et al. |
| 2003/0125790 A1 | 7/2003 | Fastovsky et al. |
| 2003/0125793 A1 | 7/2003 | Vesely |
| 2003/0130681 A1 | 7/2003 | Ungs |
| 2003/0139751 A1* | 7/2003 | Evans et al. .................. 606/127 |
| 2003/0144686 A1 | 7/2003 | Martinez et al. |
| 2003/0153943 A1 | 8/2003 | Michael et al. |
| 2003/0153945 A1 | 8/2003 | Patel et al. |
| 2003/0163159 A1 | 8/2003 | Patel et al. |
| 2003/0176888 A1 | 9/2003 | O'Connell |
| 2003/0181922 A1 | 9/2003 | Alferness |
| 2004/0010282 A1 | 1/2004 | Kusleika |
| 2004/0158273 A1 | 8/2004 | Weaver et al. |
| 2004/0186510 A1 | 9/2004 | Weaver |
| 2004/0193209 A1 | 9/2004 | Pavcnik et al. |
| 2004/0230220 A1 | 11/2004 | Osborne et al. |
| 2005/0165441 A1 | 7/2005 | McGuckin, Jr. et al. |
| 2005/0165442 A1 | 7/2005 | Thinnes, Jr. et al. |
| 2005/0251199 A1 | 11/2005 | Osborne et al. |
| 2005/0267513 A1 | 12/2005 | Osborne et al. |
| 2005/0267514 A1* | 12/2005 | Osborne et al. .............. 606/200 |
| 2006/0069406 A1 | 3/2006 | Hendriksen et al. |
| 2006/0100660 A1 | 5/2006 | Osborne et al. |
| 2006/0178695 A1* | 8/2006 | Decant et al. ................ 606/200 |
| 2007/0005095 A1 | 1/2007 | Osborne et al. |
| 2007/0208370 A1* | 9/2007 | Hauser ..................... A61F 2/01 |
| | | 606/200 |
| 2009/0312786 A1* | 12/2009 | Trask et al. .................. 606/192 |

FOREIGN PATENT DOCUMENTS

| | | |
|---|---|---|
| EP | 0270432 A1 | 6/1988 |
| EP | 0348295 A1 | 12/1989 |
| EP | 0350043 A1 | 10/1990 |
| EP | 0430848 A1 | 6/1991 |
| EP | 0437121 A2 | 7/1991 |
| EP | 0462008 A1 | 12/1991 |
| EP | 0472334 A1 | 2/1992 |
| EP | 0701800 A1 | 3/1996 |
| FR | 2587901 | 4/1987 |
| FR | 2649884 | 1/1991 |
| FR | 2672487 | 8/1992 |
| GB | 2200848 A | 8/1988 |
| GB | 2200848 B | 8/1988 |
| SU | 835447 | 6/1981 |
| SU | 1103868 A | 7/1984 |
| SU | 955912 A | 2/1988 |
| WO | WO 91/04716 | 4/1991 |
| WO | WO 91/11972 | 8/1991 |
| WO | WO 95/08567 | 3/1995 |
| WO | WO 95/27448 | 10/1995 |
| WO | WO 96/17634 | 6/1996 |
| WO | WO 01/06952 A1 | 2/2001 |
| WO | WO 03/011188 A1 | 2/2003 |
| WO | WO 2004/049973 A1 | 6/2004 |
| WO | WO 2005/072645 A1 | 8/2005 |
| WO | WO 2005/102210 A1 | 11/2005 |
| WO | WO 2005/102211 A1 | 11/2005 |
| WO | WO 2005/102212 A1 | 11/2005 |
| WO | WO 2005/102213 A1 | 11/2005 |
| WO | WO 2005/102214 A1 | 11/2005 |
| WO | WO 2006/036867 A1 | 4/2006 |

OTHER PUBLICATIONS

James Hansen, Metal That Remember, 44-47.
Morris Simon et al., Transvenous Devices for the Management of Pulmonary Emobolism, 1980, 112-121.
J.L. Kraimps et al., Annals of Vascular Surgery, Mar. 1992, 99-110.
Jean-Louis Kraimps, M.D. et al., Optimal Central Trapping (OPCETRA) Vena Cava Filter: Results of Experimental Studies, Nov. 1992, 697-699.
International Search Report—PCT/US2005/013322 (dated Sep. 23, 2005).
International Search Report—PCT/US2005/013323 (dated Sep. 23, 2005).
International Search Report—PCT/US2005/013158 (dated Oct. 7, 2005).
International Search Report—PCT/US2005/013281 (dated Oct. 7, 2005).
International Search Report—PCT/US2005/013160) dated Sep. 22, 2005).
International Search Report—PCT/US2005/034350 (dated Feb. 10, 2006).
International Search Report; PCT US2005/040299;(dated Apr. 11, 2007).

* cited by examiner

TEMPORARY VENOUS FILTER WITH ANTI-COAGULANT DELIVERY METHOD

BACKGROUND OF THE INVENTION

This invention relates to medical devices. More specifically, the invention relates to a removable vena cava clot filter that can be employed to capture and treat blood clots in the vena cava of a patient.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Although the benefits of vena cava filters have been well established, improvements may be made. For example, conventional vena cava filters commonly become off-centered or tilted with respect to the longitudinal axis of the vena cava. When such filters are tilted, their struts engage the vessel walls along their lengths. This engagement increases the likelihood that the struts of these filters will become endothelialized in the vessel walls along a substantial portion of their lengths. When the filters become endothelialized, they often cannot be removed from the vasculature of the patient, even after the condition or medical problem that required the use of the filter has passed. The vena cava filters described in U.S. Pat. No. 7,625,390, the entire contents of which are incorporated herein by reference, overcome this disadvantage of conventional vena cava filters by including a plurality of secondary struts. The secondary struts are configured to centralize the filters in the blood vessel.

Despite the advantages of the improved vena cava filter described above, further improvements to vena cava filters are still possible. For example, existing vena cava filters do not provide a means of treating captured blood clots. Therefore, the capture of especially large or numerous blood clots by existing filters may cause such filters to become clogged. Moreover, the blood clots captured by such filters may become dislodged during filter retrieval.

While it is possible to address the aforementioned risks by administering a systemic anti-coagulant, this approach also poses certain risks. For example, systemic anti-coagulant administration may be associated with an increased risk of intracranial hemorrhage. Moreover, since the effects of systemic anti-coagulant administration vary significantly from patient to patient, systemic administration requires significant and careful monitoring of the patient.

SUMMARY OF THE INVENTION

Aspects of the present invention provide a way to treat captured blood clots in a localized manner.

In one embodiment, the present invention provides a filter for capturing and treating blood clots in a blood vessel. The filter includes a hub having a distal end and a proximal end, a plurality of struts extending distally from the hub, and a tubular member disposed through the hub. The tubular member has a distal end and a proximal end. The tubular member also has a distal portion extending from the distal end of the hub to the distal end of the tubular member and a proximal portion extending from the proximal end of the hub to the proximal end of the tubular member. The distal portion of the tubular member has a plurality of perforations.

In a second embodiment, the present invention provides a filter assembly for capturing and treating blood clots in a blood vessel. The assembly includes a filter and a catheter. The filter includes a hub having a distal end and a proximal end, a plurality of struts extending distally from the hub, and a tubular member disposed through the hub. The tubular member has a distal end and a proximal end. The tubular member also has a distal portion extending from the distal end of the hub to the distal end of the tubular member and a proximal portion extending from the proximal end of the hub to the proximal end of the tubular member. The distal portion of the tubular member has a plurality of perforations. The catheter is in fluid communication with the tubular member. The catheter includes a distal end and a proximal end. The distal end of the catheter adjoins the proximal end of the tubular member.

In a third embodiment, the present invention provides a method for capturing and treating blood clots in a blood vessel. In the first step, the method involves deploying a filter assembly in the blood vessel. The assembly includes a filter and a catheter. The filter includes a hub having a distal end and a proximal end, a plurality of struts extending distally from the hub, and a tubular member disposed through the hub. The tubular member has a distal end and a proximal end. The tubular member also has a distal portion extending from the distal end of the hub to the distal end of the tubular member and a proximal portion extending from the proximal end of the hub to the proximal end of the tubular member. The distal portion of the tubular member has a plurality of perforations. The catheter is in fluid communication with the tubular member. The catheter includes a distal end and a proximal end. The distal end of the catheter adjoins the proximal end of the tubular member. In the second step, the method involves injecting a fluid into the proximal end of the catheter.

Further aspects, features, and advantages of the invention will become apparent upon consideration of the following description and the appended claims in connection with the accompanying drawings.

DETAILED DESCRIPTION OF THE INVENTION

Figure 1:
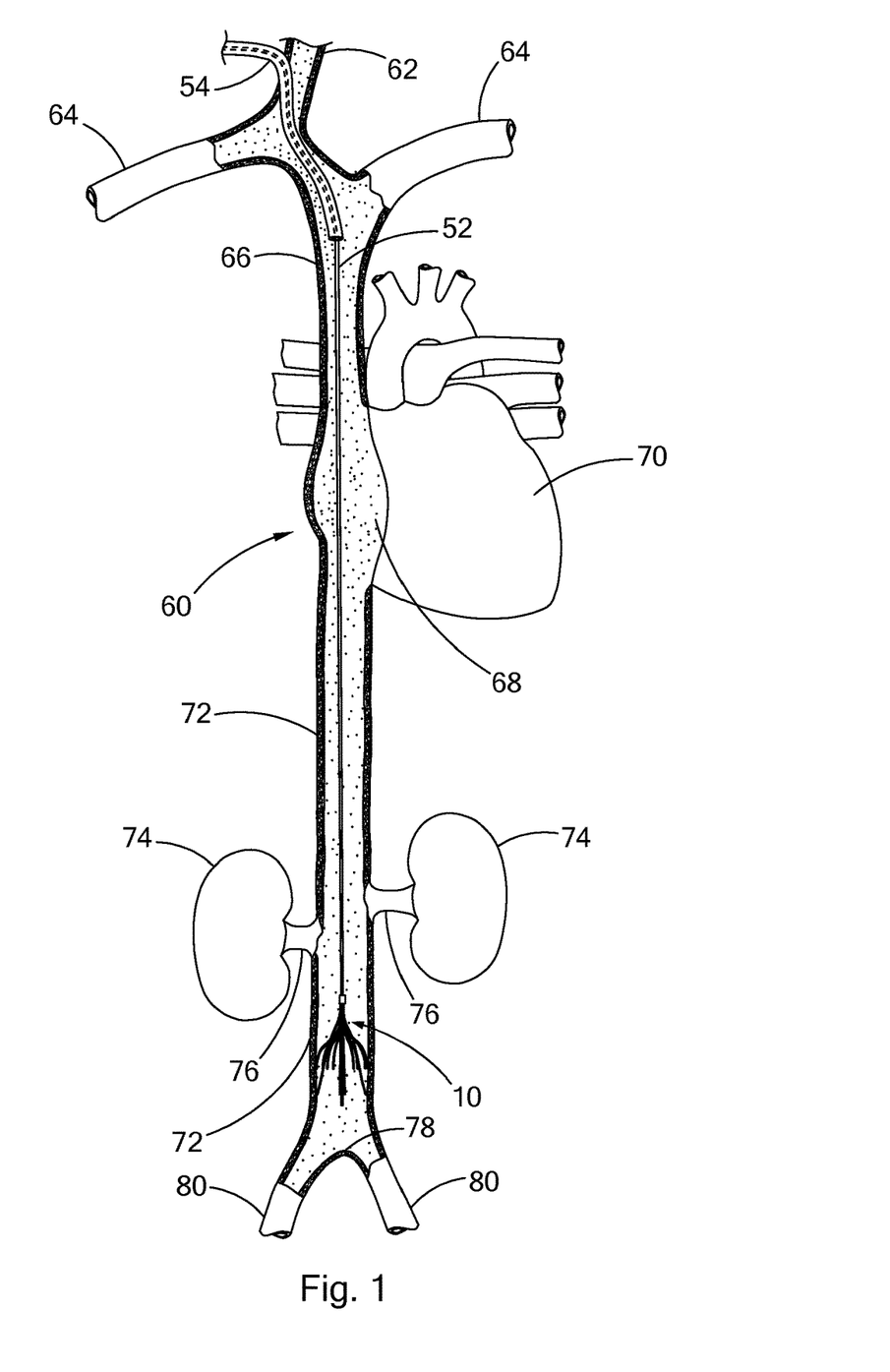
FIG. 1 is an environmental view of the filter assembly of the present invention in which the filter of the present invention is deployed in the inferior vena cava of a patient.

In accordance with one embodiment of the present invention, FIG. 1 illustrates a vena cava filter 10 deployed in the inferior vena cava 72 of a patient for the purpose of capturing and treating blood clots carried by blood flowing through the iliac veins 80 toward the heart 70 and into the pulmonary arteries. As shown, the iliac veins 80 merge at a juncture 78 into the inferior vena cava 72. The renal veins 76 from the kidneys 74 join the inferior vena cava 72 downstream of the juncture 78. The vena cava filter 10 is deployed in the inferior vena cava 72 between the juncture 78 and the renal veins 76. Preferably, the vena cava filter 10 has a length shorter than the distance between the juncture 78 and the renal veins 76. If the lower part of the filter 10 extends into the iliac veins 80, filtering effectiveness will be compromised. On the other hand, if the filter 10 crosses over the origin of the renal veins 76, the filter 10 might interfere with the flow of blood from the kidneys 74.

As further shown in FIG. 1, a catheter 52 extends proximally from the filter 10. The catheter 52 extends through the inferior vena cava 72, the right atrium 68 of the heart 70, and the superior vena 66, into the jugular vein 62. The catheter 52 exits the patient through a percutaneous incision in the jugular vein 62. As more fully discussed below, a fluid may be injected into the catheter 52 to treat blood clots captured in the filter 10.

Various embodiments of the filter 10 will be described with reference to FIGS. 2-6. In the descriptions of the various embodiments, similar numbers will be understood to refer to corresponding features of the various embodiments.

Figure 2:
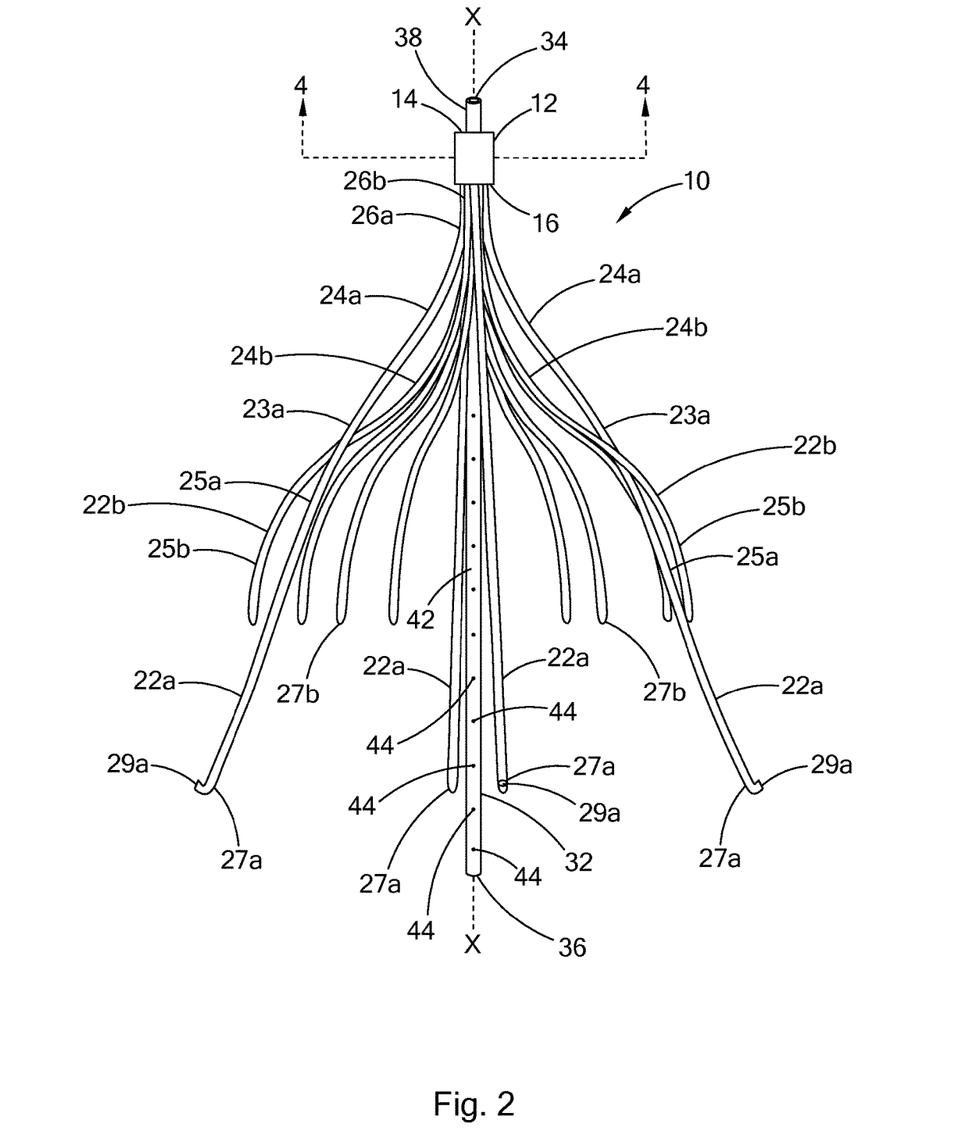
FIG. 2 is a side view of one embodiment of the filter of the present invention.

FIG. 2 illustrates the filter 10 in an expanded state. As shown in FIG. 2, the filter 10 comprises a hub 12, a plurality of struts 22a and 22b extending distally from the hub 12, and a tubular member 32 disposed through the hub 12. The hub 12 has a proximal or downstream end 14 and a distal or upstream end 16. Each strut has a first end 26a or 26b attached to the hub 12 and a second end 27a or 27b disposed distally to the hub 12. The hub 12 may attach to the struts 22a and 22b by crimping the first ends 26a and 26b of the struts 22a and 22b together along a central or longitudinal axis X of the filter 10. The hub 12 has a minimal diameter necessary to accommodate the tubular member 32 and the first ends 26a and 26b of the struts 22a and 22b.

The struts 22a and 22b are preferably formed from a wire having a round cross-section with a diameter of at least about 0.012 inches. Of course, it is not necessary that the struts have a round or near round cross-section. For example, the struts 22a and 22b could take on any shape with rounded edges to maintain non-turbulent blood flow therethrough.

The struts 22a and 22b are configured to move between an expanded state for capturing and treating blood clots in the blood vessel and a collapsed state for filter delivery and retrieval. Preferably, the struts 22a and 22b are formed of a superelastic material, such as stainless steel wire, nitinol, cobalt-chromium-nickel-molybdenum-iron alloy, cobalt-chrome alloy, or any other suitable superelastic material that will result in a self-opening or self-expanding filter. The hub 12 is preferably made of the same material as the struts 22a and 22b to minimize the possibility of galvanic corrosion or changes in the material due to welding.

As noted above, the tubular member 32 is disposed through the hub 12, preferably along the central or longitudinal axis X of the filter 10. Preferably, the tubular member 32 is fixedly attached to the hub 12. The tubular member 32 has a proximal or third end 34, which is disposed proximally to the proximal end 14 of the hub 12, and a distal or fourth end 36, which is disposed distally to the distal end 16 of the hub 12. Preferably, the distal end 36 of the tubular member 32 is disposed distally to the second ends 27a and 27b of the struts 22a and 22b.

The tubular member 32 includes a distal portion 42, defined as that portion of the tubular member disposed between the distal end 16 of the hub 12 and the distal end 36 of the tubular member 32. The tubular member 32 also includes a proximal portion 38, defined as that portion of the tubular member 32 disposed between the proximal end 14 of the hub 12 and the proximal end 34 of the tubular member 32. As more fully shown in FIG. 3, the tubular member 32 has a lumen 46, which provides for fluid communication between the proximal portion 38 of the tubular member 32 and the distal portion 42 of the tubular member 32 through the hub 12. The distal end 36 of the tubular member 32 may be open or closed. In a preferred embodiment, the distal end 36 of the tubular member 32 is closed.

Figure 3:
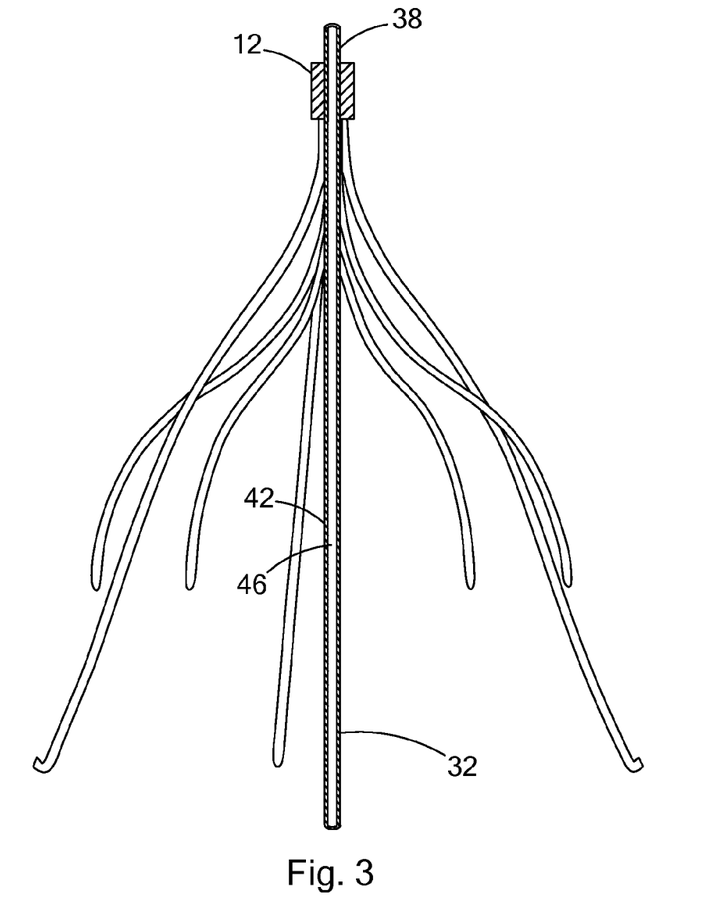
FIG. 3 is a cross-sectional view of the filter in FIG. 2.

The tubular member 32 may be constructed from any biocompatible material. For example, the tubular member 32 may be constructed from a rigid material, such as stainless steel, nitinol, rigid plastic (e.g., polytetrafluoroethylene), or any other suitable rigid material. Alternatively, the tubular member 32 may be constructed from a flexible material, such as silicone, polytetrafluoroethylene, urethane, or any other suitable flexible material. The lumen 46 of the tubular member 32 preferably has a diameter between 0.0014 and 0.0035 inches, and more preferably has a diameter between 0.0016 and 0.0020 inches.

Figure 4:
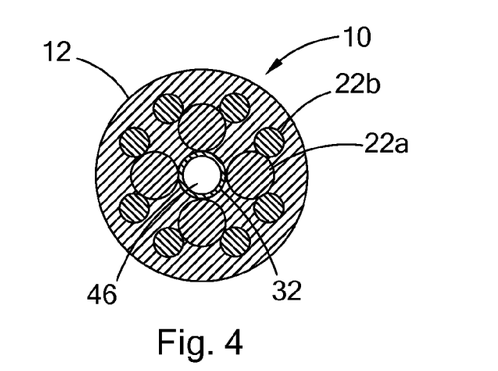
FIG. 4 is a cross-sectional view of the hub of the filter in FIG. 2 taken along line 4-4.
Figure 5A:
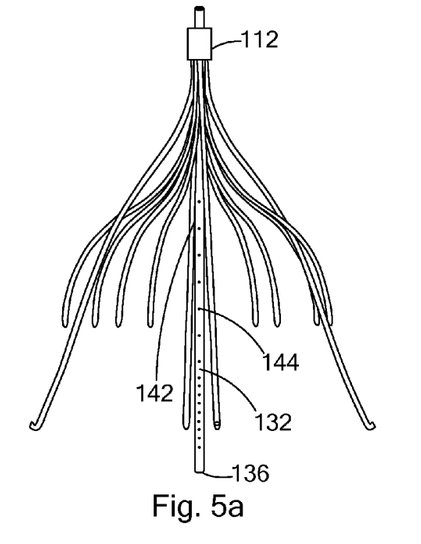
FIG. 5a is a side view of another embodiment of the filter of the present invention.
Figure 5B:
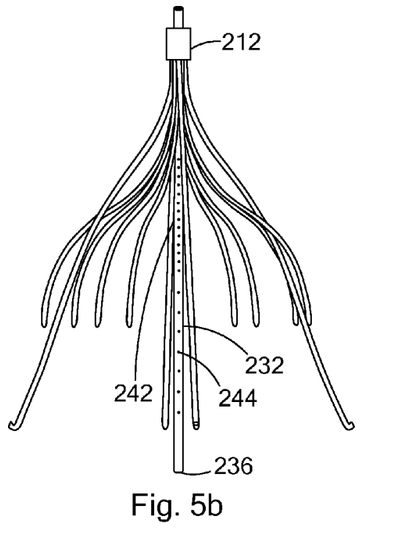
FIG. 5b is a side view of still another embodiment of the filter of the present invention.
Figure 5C:
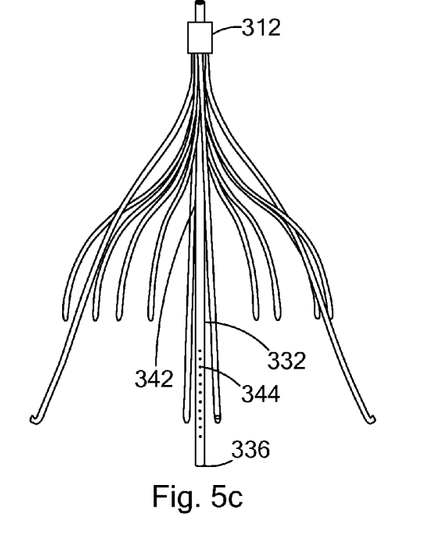
FIG. 5c is a side view of yet another embodiment of the filter of the present invention.
Figure 5D:
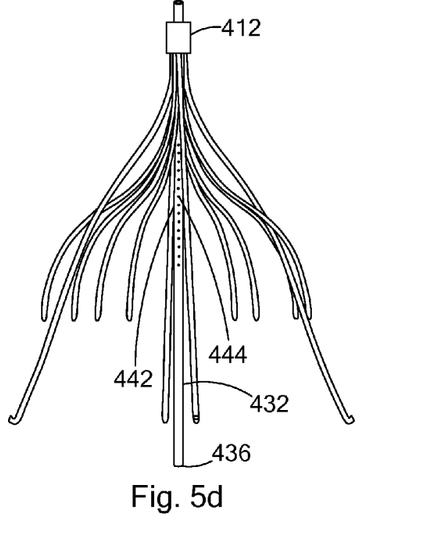
FIG. 5d is a side view of still yet another embodiment of the filter of the present invention.

FIG. 4 illustrates a cross-sectional view of the filter 10 of FIG. 2 at the hub 12. As shown, the hub 12 houses the first ends of the plurality of struts 22a and 22b. FIG. 4 also depicts the tubular member 32 disposed through the hub 12.

As shown in FIG. 2, the distal portion 42 of the tubular member 32 includes a plurality of perforations 44. The perforations 44 are small holes in the wall of the tubular member 32. The perforations 44 are sufficiently large to allow a fluid introduced into the lumen 46 of the tubular member 32 to escape from the lumen 46 through the perforations 44. Preferably, the perforations have a diameter between 0.0002 and 0.0015 inches. The perforations 44 may take any shape, including circular, elliptical, square, rectangular, or any other suitable shape. Preferably, the perforations are circular or elliptical. More preferably, the perforations are circular. Depending on the material from which the tubular member 32 is constructed, the perforations 44 may be introduced into the wall of the tubular member 32 by a variety of methods, including laser drilling, electric discharge machining (EDM), or any other suitable method.

In various embodiments of the present invention, the perforations 44 are selectively placed along the length, and about the circumference, of the distal portion 42 of the tubular member 32. In one embodiment, shown in FIG. 2, the perforations 44 are approximately evenly spaced along the entire length of the distal portion 42 of the tubular member 32. In another embodiment, shown in FIG. 5a, the perforations 144 occur along the entire length of the distal portion 142 of the tubular member 132, but the concentration of perforations 144 is highest near the distal end 136 of the tubular member 132. In still another embodiment, shown in FIG. 5b, the perforations 244 occur along the entire length of the distal portion 242 of the tubular member 232, but the concentration of perforations 244 is highest near the hub 212. In yet another embodiment, shown in FIG. 5c, the perforations 344 only occur near the distal end 336 of the tubular member 332. In still yet another embodiment, shown in FIG. 5d, the perforations 444 only occur near the hub 412. In addition, the perforations 44 may be selectively placed either on a single side, on a plurality of sides, or about the entire circumference of the tubular member 32. Furthermore, the perforations 44 may vary in shape, size, or shape and size along the length, and about the circumference, of the distal portion 42 of the tubular member 32. Preferably, the perforations 44 increase in size along the length of the distal portion 42 of the tubular member 32, such that the smallest perforations 44 are disposed near the hub 12, and the largest perforations 44 are disposed near the distal end 36 of the tubular member 32. The perforations may also be selectively placed in any other appropriate pattern without falling beyond the scope or spirit of the present invention.

In some embodiments of the present invention, such as that shown in FIG. 2, the plurality of struts comprises a plurality of primary struts 22a and a plurality of secondary struts 22b.

Each primary strut 22a includes an arcuate segment 23a having a soft S-shape. Each arcuate segment 23a is formed with a first curved portion 24a that is configured to softly bend away from the longitudinal or central axis X of the filter 10 and a second curved portion 25a that is configured to softly bend toward the axis X of the filter 10. Due to the soft bends of each arcuate segment 23a, a prominence or a point of inflection on the primary strut 22a is substantially avoided to aid in non-traumatically engaging the vessel wall.

As shown in FIG. 2, the primary struts 22a terminate at anchoring hooks 29a. When the filter 10 is deployed in a blood vessel, the anchoring hooks 29a engage the walls of the blood vessel in a first radial plane to secure the filter in the blood vessel. Thus, the anchoring hooks 29a prevent the filter 10 from migrating from the delivery location in the blood vessel where it has been deployed. The primary struts 22a have sufficient spring strength that, when the filter is deployed, the anchoring hooks 29a will anchor into the vessel wall.

The primary struts 22a are configured to move between an expanded state for engaging the anchoring hooks 29a with the wall of the blood vessel and a collapsed state for filter delivery and retrieval. In the expanded state, each arcuate segment 23a extends arcuately along a longitudinal axis and linearly relative to a radial axis from the first end 26a to the anchoring hook 29a. The primary struts 22a extend linearly relative to the radial axis to avoid entanglement with other struts 22a and 22b.

The primary struts 22a are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm. The length of the filter 10 is defined as the distance, along the longitudinal axis X, from the distal end 16 of the hub 12 to the point where the first radial plane intersects the longitudinal axis X.

As shown in FIG. 2, the filter 10 further includes a plurality of secondary struts 22b. In the embodiment depicted in FIG. 2, each primary strut 22a has two secondary struts 22b in side-by-side relationship with the primary strut 22a. The secondary struts 22b independently extend from connected first ends 26b to free second ends 27b to centralize the filter 10 in the expanded state in a blood vessel. Each of the secondary struts 22b is formed of a first arc 24b and a second arc 25b. The first arc 24b extends from the connected first end 26b away from the longitudinal axis X. The second arc 25b extends from the first arc 24b towards the longitudinal axis X and terminates at a free second end 27b without a hook. As shown, each secondary strut 22b extends arcuately along a longitudinal axis and linearly relative to a radial axis from the connected first end 26b to the free second end 27b. Each secondary strut 22b freely extends from the hub 12, avoiding contact with other struts 22a and 22b. This configuration lessens the likelihood of entanglement.

When allowed to expand freely, the free second ends 27b of the secondary struts 22b expand radially outwardly to a diameter of about 25 mm to 45 mm to engage the vessel wall. For example, the secondary struts 22b may expand radially outwardly to a diameter of between about 35 mm and 45 mm. The second arcs 25b and the free second ends 27b engage the wall of a blood vessel, the free second ends 27b defining a second radial plane. As a result, the filter 10 has two layers struts longitudinally engaging the wall of the blood vessel in two different radial planes. The secondary struts 22b function to stabilize the position of the filter 10 about the center of the blood vessel in which it is deployed.

In the embodiment shown in FIG. 2, each arcuate segment 23a has an absolute tensile strength of between about 285,000 pounds per square inch (psi) and 330,000 psi. Each anchoring hook 29a is integral with the arcuate segment 23a and has the same thickness and absolute tensile strength as the arcuate segment 23a. Each secondary strut 22b has an absolute tensile strength of between about 285,000 psi and 330,000 psi.

Figure 6:
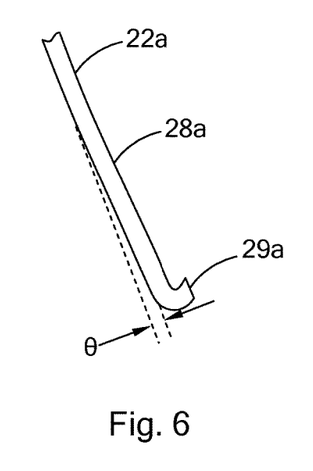
FIG. 6 is an enlarged view of the distal portion of a primary strut of the filter in FIG. 2.

FIG. 6 illustrates a distal portion of a primary strut 22a of the filter 10. As shown, the primary struts 22a include a distal bend 28a extending outwardly radially from the longitudinal axis X. The distal bend 28a may extend outwardly at an angle θ between about 0.5 degree and 2.0 degrees, preferably 1.0 degree. The distal bend 28a allows the filter 10 to filter blood clots effectively at a smaller inside diameter of blood vessel than otherwise would be possible while maintaining the ability to collapse for delivery or retrieval.

As most clearly shown in FIG. 4, the filter of FIG. 2 comprises four primary struts 22a and eight secondary struts 22b. FIG. 4 further depicts the configuration of the primary struts 22a, secondary struts 22b, and tubular member 32. In this embodiment, each primary strut 22a is spaced between two secondary struts 22b. Of course, any suitably desired number of primary struts 22a may be spaced between any other suitably desired number of secondary struts 22b without falling beyond the scope or spirit of the present invention.

Figure 7:
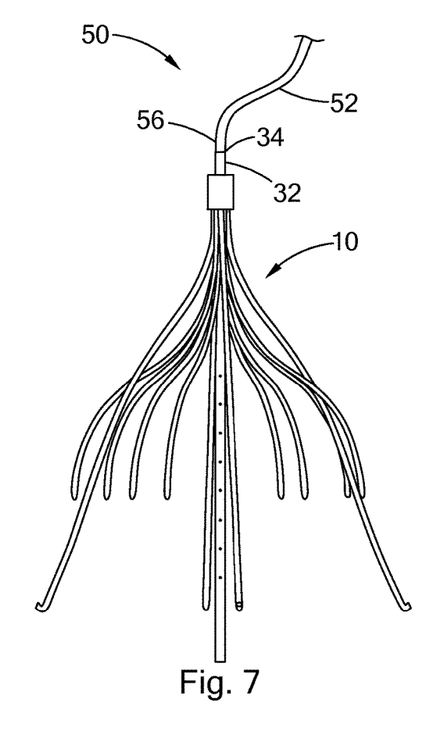
FIG. 7 is a side view of the filter assembly of the present invention.

Referring now to FIG. 7, the filter assembly 50 of the present invention comprises the filter 10 (as described above) and a catheter 52 in fluid communication with the tubular member 32 of the filter 10. The catheter 52 includes a distal or fifth end 56 and a proximal or sixth end (not shown). The distal end 56 of the catheter 52 adjoins the proximal end 34 of the tubular member 32.

Preferably, the catheter 52 is constructed from a flexible material, such as silicone, Teflon, urethane, or any other suitable flexible material. The distal end 56 of the catheter 52 may be fixedly attached to the proximal end 34 of the tubular member 32, or the catheter 52 may be integrally formed with the tubular member 32. If the catheter 52 is fixedly attached to the tubular member 32, the attachment may be accomplished by adhesive bonding, thermal bonding, clamping, or any other suitable means of attachment.

When the filter assembly 50 is in use, the proximal end of the catheter 52 is disposed outside the patient's vasculature. The proximal end of the catheter 52 may be connected to a fluid manifold. In this configuration, fluid may be injected into the catheter to treat blood clots captured in the filter 10 (as discussed below).

Figure 8:
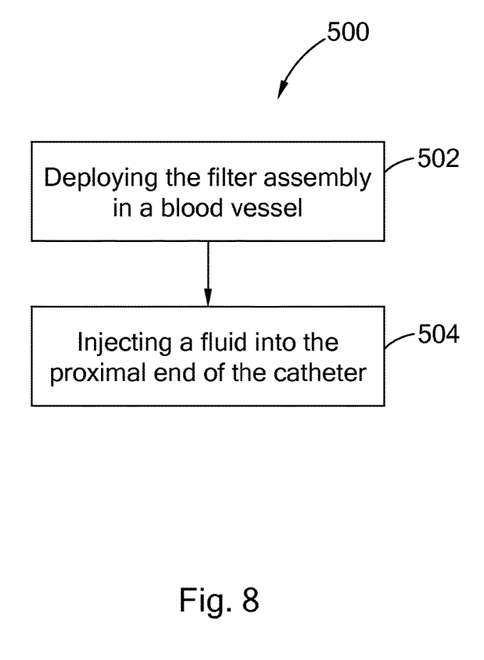
FIG. 8 is a flow chart of a method for capturing and treating blood clots in a blood vessel in accordance with the present invention.

FIG. 8 depicts a flow chart illustrating one method 500 for capturing and treating blood clots in a blood vessel using the filter assembly 50 of the present invention. As indicated in block 502, the method 500 comprises deploying the filter assembly 50 in a patient's vasculature, preferably such that the filter 10 is disposed in the patient's inferior vena cava. As indicated in block 504, the method 500 further comprises injecting a fluid into the proximal end of the catheter 52 to treat blood clots captured in the filter 10.

Figure 9:
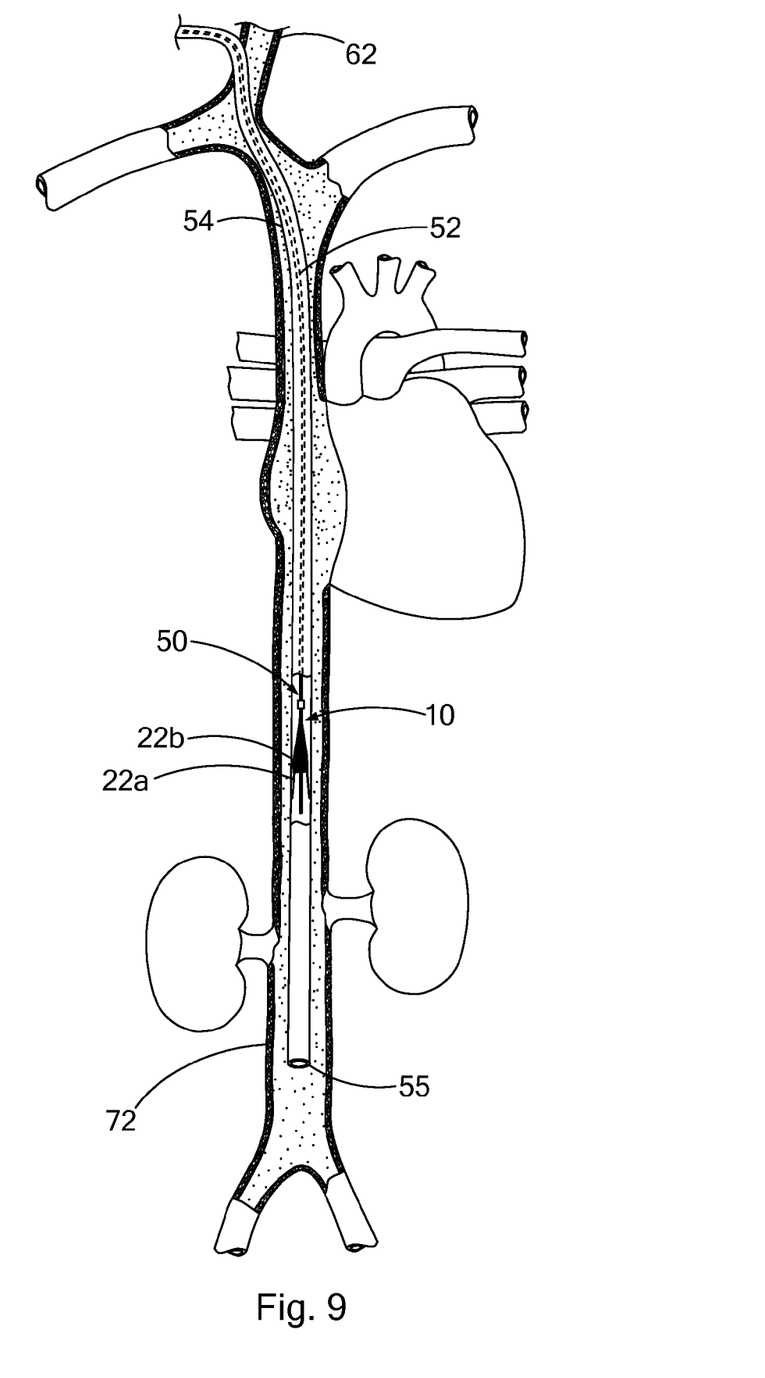
FIG. 9 is an environmental view illustrating the delivery of the filter assembly of the present invention into the inferior vena cava of a patient.

The method outlined in FIG. 8 will be more fully described with reference to FIGS. 9-13. To deploy the filter assembly 50, a delivery tube 54 is percutaneously inserted into the patient's jugular vein 62 and through the patient's vasculature such that the distal or seventh end 55 of the delivery tube 54 is disposed at the desired location of deployment of the filter 10 in the patient's inferior vena cava 72 (FIG. 9). A wire guide (not shown) is preferably used to guide the delivery tube 54 to the location of deployment.

Any suitable delivery tube 54 may be used to deploy the filter assembly 50. Preferably, the delivery tube is constructed of polytetrafluoroethylene (PTFE), reinforced PTFE, polyether ether ketone (PEEK), or any other suitable material. It is also preferred that the delivery tube has an inside diameter of between about 4.5 French and 16 French, more preferably between about 6.5 French and 14 French.

The filter 10 of the filter assembly 50 is inserted into the proximal or eighth end of the delivery tube 54 with the second ends 27a and 27b of the struts 22a and 22b leading and the catheter 52 trailing. A pusher wire (not shown) having a pusher member at its distal end may be used to advance the filter 10 through the delivery tube 54 toward the location of deployment. As the filter 10 is advanced through the delivery tube 54, the catheter 52 is fed into the proximal end of the delivery tube 54. In FIG. 9, a portion of the delivery tube 54 has been cut away, revealing the filter 10.

Figure 10:
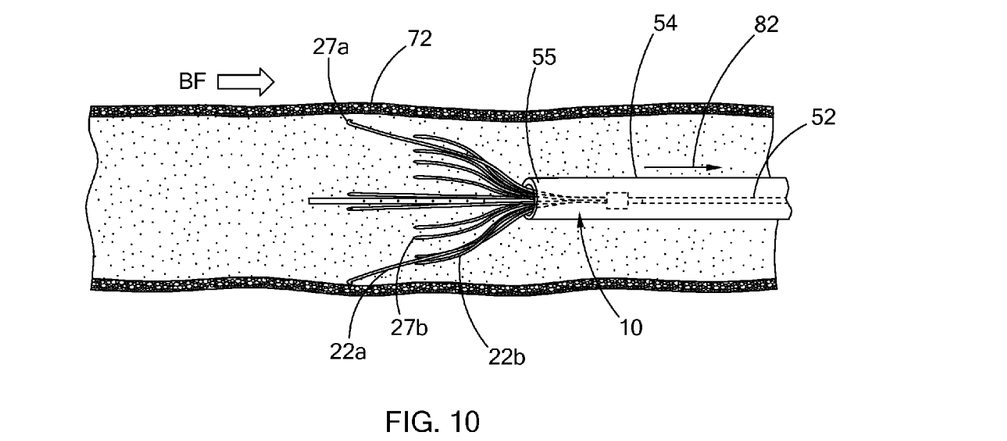
FIG. 10 is a cross-sectional view of a blood vessel depicting the deployment of the filter of the present invention.
Figure 11:
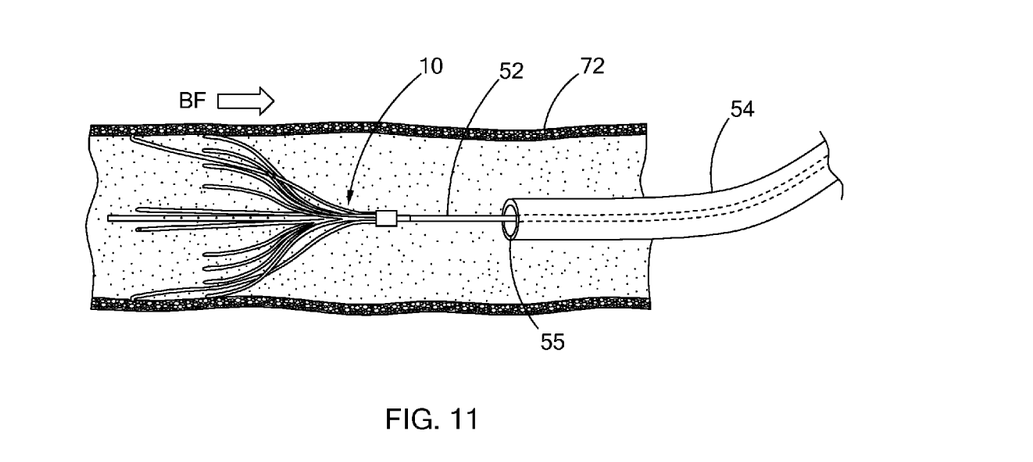
FIG. 11 is a cross-sectional view of a blood vessel depicting the filter of the present invention fully deployed.

Referring now to FIG. 10, when the second ends 27a and 27b of the struts 22a and 22b reach the distal end 55 of the delivery tube 54, the pusher wire (not shown) may be used to hold the filter at the location of deployment while the delivery tube 54 is retracted in the direction indicated by arrow 82. As the struts 22a and 22b emerge from the distal end 55 of the delivery tube 54 at the location of deployment, the struts 22a and 22b expand to engage the wall of the inferior vena cava 72. After the filter 10 has fully emerged from the distal end 55 of the delivery tube 54, as shown in FIG. 11, the delivery tube 54 and the pusher wire (not shown) may be removed from the patient's vasculature.

Figure 12:
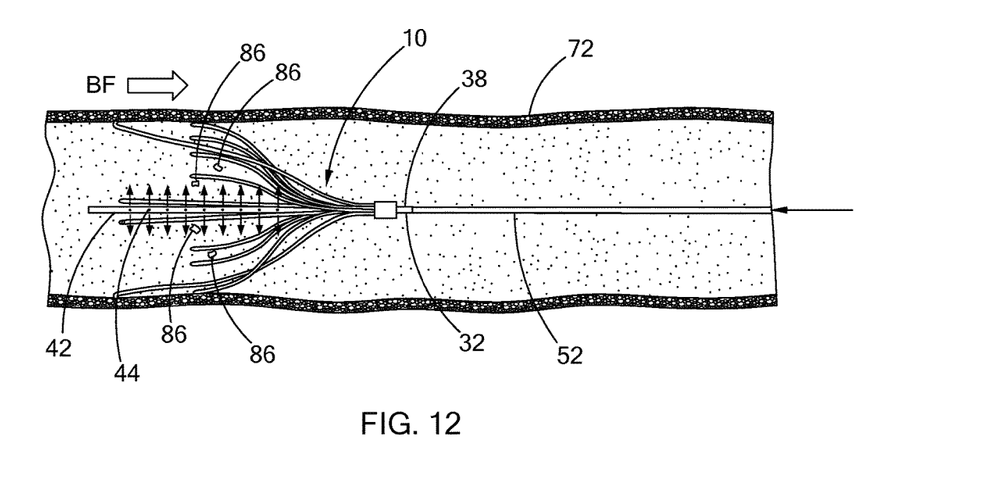
FIG. 12 is a cross-sectional view of a blood vessel depicting the treatment of emboli captured in the filter of the present invention.

In its deployed and expanded state, illustrated in FIG. 12, the filter 10 captures blood clots 86 carried by the blood flowing through the inferior vena cava 72. To treat the blood clots 86 captured in the filter 10, a fluid is injected into the proximal end (not shown) of the catheter 52 outside of the patient's vasculature. The fluid flows through the catheter 52, through the proximal portion 38 of the tubular member 32, and into the distal portion 42 of the tubular member 32. The fluid passes through the perforations 44 in the distal portion 42 of the tubular member 32 and into the blood stream.

As will be understood by those having skill in the relevant art, a variety of fluids, such as drugs, contrast agents, dyes, or other suitable fluids, may be employed to treat blood clots captured in the filter 10. Preferably, the fluid is a drug, such as an anti-coagulant, a direct thrombin inhibitor (e.g., bivalirudin), an anti-platelet drug (e.g., cilostazol), or any other suitable drug. More preferably, the fluid is an anti-coagulant, such as heparin, or any other suitable anti-coagulant. Most preferably, the fluid is heparin.

In accordance with the method illustrated in FIG. 8 and described above, the treatment of blood clots captured in the filter 10 may involve a single treatment, repeated treatments, or a continuous treatment over a period of time. Preferably, the fluid is injected continuously over a period of time into the proximal end of the catheter 52, effecting continuous treatment of the captured blood clots. More preferably, the fluid is injected continuously over a period of two to six days. However, any other suitable treatment schedule may be employed without falling beyond the scope or spirit of the present invention.

Figure 13:
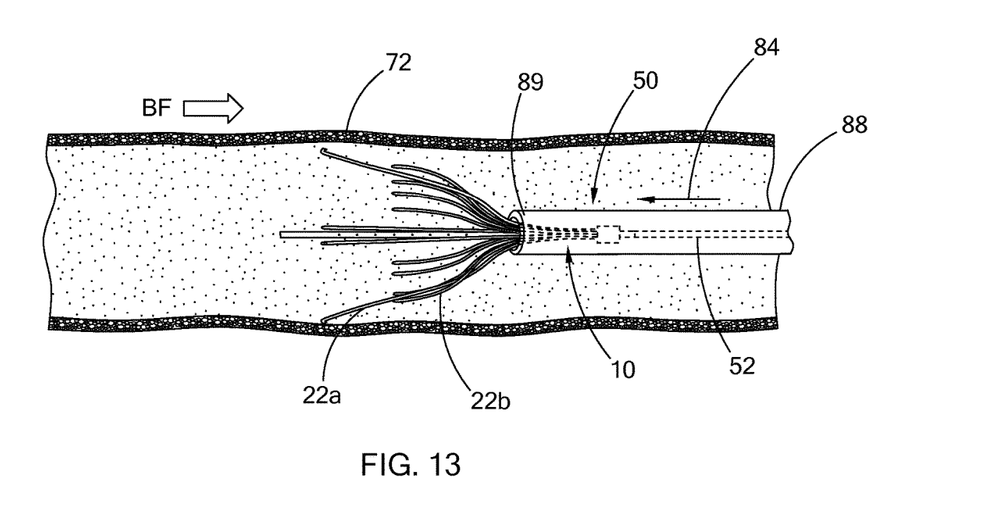
FIG. 13 is a cross-sectional view of a blood vessel depicting the retrieval of the filter of the present invention.

After the risk of embolism has subsided, and after the treatment of blood clots captured in the filter 10 has been completed, the filter assembly 50 may be removed from the patient's vasculature as shown in FIG. 13. A retrieval tube 88 is advanced over the catheter 52 to the filter 10. When the distal or ninth end 89 of the retrieval tube reaches the filter 10, the practitioner removing the filter assembly 50 holds the filter 10 in a fixed position by applying tension to the proximal end (not shown) of the catheter 52 outside of the patient's vasculature. As the distal end 89 of the retrieval tube 88 engages the struts 22a and 22b, and as the retrieval tube 88 is advanced over the struts 22a and 22b in the direction indicated by the arrow 84, the struts 22a and 22b disengage from the wall of the inferior vena cava 72 and fold down to their collapsed state inside the retrieval tube 88. Once the filter 10 is completely housed inside the retrieval tube 88, the entire assembly may be withdrawn from the patient's vasculature. As will be understood by those having skill in the art, the delivery tube 54 may also be used as the retrieval tube 88. In the alternative, the retrieval tube 88 may be constructed in a manner similar to the delivery tube 54 as described above.

While the present invention has been described in terms of certain preferred embodiments, it will be understood that the invention is not limited to the disclosed embodiments, as those having skill in the art may make various modifications without departing from the scope of the following claims.

What is claimed is:

1. A filter for capturing and treating blood clots in a blood vessel, the filter comprising:
   only one hub having a distal end and a proximal end;

a plurality of struts extending distally from the distal end of the hub and having distal strut ends located radially outward from the hub in an expanded configuration; and a tubular member disposed through the hub, the tubular member having a distal end and a proximal end and extending along a central longitudinal axis when the struts are in the expanded configuration, the tubular member having a distal portion extending from the distal end of the hub to the distal end of the tubular member, an intermediate portion extending through the hub from the proximal end of the hub to the distal end of the hub, and a proximal portion extending from the proximal end of the hub to the proximal end of the tubular member, the distal portion, the intermediate portion, and the proximal portion being in fluid communication via a lumen extending inside the tubular member, the distal portion of the tubular member having a plurality of perforations, and the proximal end being free of perforations and having an opening in communication with the lumen and with the perforations, the opening being located relative to the hub longitudinally opposite the plurality of struts and configured to be sealingly attached to a catheter to place a lumen of the catheter in fluid communication with the lumen of the tubular member, the distal end of the tubular member being closed.

2. The filter of claim 1, wherein the tubular member is fixedly attached to the hub.

3. The filter of claim 1, wherein each strut has a first end attached to the hub and a second end, and wherein the distal end of the tubular member is disposed distally from the second ends of the plurality of struts.

4. The filter of claim 1, wherein the tubular member is constructed from a rigid material.

5. The filter of claim 1, wherein the tubular member is constructed from a flexible material.

6. The filter of claim 1, wherein the perforations are selectively placed on the distal portion of the tubular member.

7. The filter of claim 1, wherein the perforations have a plurality of sizes or shapes.

8. The filter of claim 1, wherein the plurality of struts comprise:

a plurality of primary struts having first ends attached to the hub along a longitudinal axis, each primary strut extending arcuately along the longitudinal axis and linearly radially, each primary strut including an arcuate segment having a first absolute tensile strength, the arcuate segment including a first curved portion and a second curved portion, the first curved portion extending from the first end away from the longitudinal axis, the second curved portion extending from the first curved portion toward the longitudinal axis and terminating at an anchoring hook, the anchoring hook being integral with the arcuate segment and having the same thickness as the arcuate segment; and a plurality of secondary struts freely spaced between the primary struts and having connected ends attached to the hub along the longitudinal axis, each secondary strut freely extending from the connected end to a free end avoiding contact with other secondary struts and primary struts, each secondary strut extending arcuately along the longitudinal axis and linearly radially, each secondary strut including a first arc and a second arc, the first arc extending from the connected end away from the longitudinal axis, the second arc extending from the first arc toward the longitudinal axis and terminating at the free end without a hook, each secondary strut having a second absolute tensile strength.

9. A filter assembly for capturing and treating blood clots in a blood vessel, the assembly comprising:

a filter comprising:
only one hub having a distal end and a proximal end;
a plurality of struts extending distally from the distal end of the hub and having distal strut ends located radially outward from the hub in an expanded configuration; and
a tubular member disposed through the hub, the tubular member having a distal end and a proximal end and extending along a central longitudinal axis when the struts are in the expanded configuration; and
the tubular member having a distal portion extending from the distal end of the hub to the distal end of the tubular member, an intermediate portion extending through the hub from the proximal end of the hub to the distal end of the hub, and a proximal portion extending from the proximal end of the hub to the proximal end of the tubular member, the distal portion, the intermediate portion, and the proximal portion being in fluid communication via a lumen extending inside the tubular member, the distal portion of the tubular member having a plurality of perforations, and the proximal end having an opening in communication with the lumen and with the perforations, wherein the proximal portion is free of perforations, the distal end of the tubular member being closed; and a catheter in fluid communication with the lumen of the tubular member, the catheter having a distal end and a proximal end, the distal end of the catheter sealingly adjoining the proximal end of the tubular member, the proximal end of the tubular member being located relative to the hub longitudinally opposite the plurality of struts.

10. The filter assembly of claim 9, wherein the distal end of the catheter is fixedly attached to the proximal end of the tubular member.

11. The filter assembly of claim 9, wherein the catheter is formed integrally with the tubular member.

12. The filter assembly of claim 9, wherein the catheter is constructed from a flexible material.

13. The filter assembly of claim 9, further comprising a fluid manifold attached to the proximal end of the catheter.

14. A method for capturing and treating blood clots in a blood vessel, the method comprising the steps of:

deploying a filter assembly in the blood vessel, the filter assembly comprising:
a filter comprising:
only one hub having a distal end and a proximal end;
a plurality of struts extending distally from the distal end of the hub and having distal strut ends located radially outward from the hub in an expanded configuration; and
a tubular member passing through the hub, the tubular member having a distal end and a proximal end and extending along a central longitudinal axis when the struts are in the expanded configuration, the tubular member having a distal portion extending from the distal end of the hub to the distal end of the tubular member, an intermediate portion extending through the hub from the proximal end of the hub to the distal end of the hub, and a proximal portion extending from the proximal end of the hub to the proximal end of the tubular member, the distal portion, the intermediate portion, and the proximal portion being in fluid communication via a lumen extending inside the tubular member, the distal portion of the tubular member having a plurality of perforations, wherein the proximal portion is free of perforations, and the proximal end having an opening in fluid communication with the lumen and with the perforations, the distal end of the tubular member being closed; and a catheter in fluid communication with the lumen of the tubular member, the catheter having a distal end and a proximal end, the distal end of the catheter being attached to the proximal end of the tubular member located relative to the hub longitudinally opposite the struts, the proximal end of the catheter residing outside the blood vessel;

injecting a fluid into the proximal end of the catheter.

15. The method of claim 14, wherein the fluid is a drug.

16. The method of claim 15, wherein the drug is an anti-coagulant.

17. The method of claim 16, wherein the anti-coagulant is heparin.

18. The method of claim 14, wherein the fluid is injected continuously over a period of time.

19. The method of claim 18, wherein the period of time is between two and six days.

* * * * *